US011299768B2

(12) United States Patent
Cazalis et al.

(10) Patent No.: US 11,299,768 B2
(45) Date of Patent: Apr. 12, 2022

(54) METHODS FOR DETERMINING A PATIENT'S SUSCEPTIBILITY OF CONTRACTING A NOSOCOMIAL INFECTION AND FOR ESTABLISHING A PROGNOSIS OF THE PROGRESSION OF SEPTIC SYNDROME (75) Inventors: Marie-Angelique Cazalis, Vaulx en Velin (FR); Alain Lepape, Saint-Genis Laval (FR); Guillaume Monneret, Lyons (FR); Bruno Mougin, Lyons (FR); Alexandre Pachot, Sulignat (FR)

(73) Assignees: BIOMERIEUX, Marcy L'Etoile (FR); HOSPICES CIVILS DE LYON, Lyons (FR)

( * ) Notice: Subject to any disclaimer, the term of this patent is extended or adjusted under 35 U.S.C. 154(b) by 0 days.

(21) Appl. No.: 13/140,678

(22) PCT Filed: Jan. 18, 2010

(86) PCT No.: PCT/FR2010/050070
§ 371 (c)(1),
(2), (4) Date: Jun. 17, 2011

(87) PCT Pub. No.: WO2010/082004
PCT Pub. Date: Jul. 22, 2010

(65) Prior Publication Data
US 2011/0250592 A1  Oct. 13, 2011

(30) Foreign Application Priority Data

Jan. 19, 2009 (FR) .................................. 0950305
Jan. 19, 2009 (FR) .................................. 0950306

(51) Int. Cl.
| C12Q 1/6809 | (2018.01) |
| C12Q 1/686 | (2018.01) |
| C12Q 1/6886 | (2018.01) |
| C12Q 1/6876 | (2018.01) |
| C12Q 1/6865 | (2018.01) |
| C12Q 1/6813 | (2018.01) |
| C12Q 1/6883 | (2018.01) |

(52) U.S. Cl.
CPC .......... *C12Q 1/6809* (2013.01); *C12Q 1/686* (2013.01); *C12Q 1/6813* (2013.01); *C12Q 1/6865* (2013.01); *C12Q 1/6876* (2013.01); *C12Q 1/6883* (2013.01); *C12Q 1/6886* (2013.01); *C12Q 2521/107* (2013.01); *C12Q 2545/10* (2013.01); *C12Q 2561/113* (2013.01); *C12Q 2600/118* (2013.01); *C12Q 2600/158* (2013.01)

(58) Field of Classification Search
CPC .... C12Q 1/6809; C12Q 1/6883; C12Q 1/686; C12Q 1/6876; C12Q 1/6865; C12Q 1/6813; C12Q 2600/118; C12Q 2600/158; G01N 2800/26
See application file for complete search history.

(56) References Cited

U.S. PATENT DOCUMENTS

| 4,672,040 | A | 6/1987 | Josephson |
| 5,234,809 | A | 8/1993 | Boom et al. |
| 5,399,491 | A | 3/1995 | Kacian et al. |
| 5,750,338 | A | 5/1998 | Collins et al. |
| 2003/0050470 | A1* | 3/2003 | An .......................... C07H 21/00 536/24.3 |
| 2003/0092009 | A1* | 5/2003 | Palm ................................ 435/6 |
| 2003/0119049 | A1* | 6/2003 | Lorincz et al. ................... 435/6 |
| 2004/0152107 | A1* | 8/2004 | Altar .................. G01N 33/6896 435/6.14 |
| 2004/0258669 | A1* | 12/2004 | Dzau ..................... C12N 5/0663 424/93.21 |
| 2005/0064506 | A1 | 3/2005 | Bergmann |
| 2005/0181439 | A1* | 8/2005 | Choi .................. C07K 14/3156 435/6.15 |
| 2006/0008804 | A1* | 1/2006 | Chibout et al. .................... 435/6 |
| 2006/0068433 | A1* | 3/2006 | Godfrey ............... C12Q 1/6851 435/6.18 |
| 2007/0092911 | A1 | 4/2007 | Buechler et al. |
| 2007/0160528 | A1 | 7/2007 | Culver |
| 2007/0292874 | A1* | 12/2007 | Souza et al. ...................... 435/6 |
| 2008/0070235 | A1 | 3/2008 | Russwurm et al. |
| 2010/0105084 | A1* | 4/2010 | Payen De La Garanderie et al. .. 435/7.92 |
| 2011/0287433 | A1* | 11/2011 | Payen de La Garanderie et al. ... 435/6.12 |

FOREIGN PATENT DOCUMENTS

| EP | 1 318 403 A1 | 6/2003 |
| EP | 1 950 310 A1 | 7/2008 |
| WO | WO 90/06995 A1 | 6/1990 |

(Continued)

OTHER PUBLICATIONS

Vogl et al. Nature Medicine (2007) 13(9): 1042-1049.*
Van Zoelen et al. American Journal of Respiratory and Critical Care Medicine (2009) 180: 1098-1106.*
Fontaine et al. Abstract P56, "Delayed increased S100A9 mRNA predicts hospital-acquired infection after septic shock", Critical Care, vol. 13, Suppl 4, 2009; Sepsis 2009, Amsterdam, the Netherlands, Nov. 11-14, 2009 (published online Nov. 11, 2009).*

(Continued)

*Primary Examiner* — Angela M. Bertagna
(74) *Attorney, Agent, or Firm* — Oliff PLC (57) ABSTRACT A method for determining a patient's susceptibility of contracting a nosocomial infection that includes obtaining a biological sample from the patient and extracting biological material from the biological sample; preparing a specific reagent of an expression product of at least one target gene selected from S100A9 and S100A8 target genes; and determining the expression of at least one of the target genes S100A9 and S100A8, where overexpression relative to a specified threshold value indicates susceptibility of contracting a nosocomial infection.

8 Claims, 2 Drawing Sheets
Specification includes a Sequence Listing.

(56) References Cited

FOREIGN PATENT DOCUMENTS

| WO | WO 91/19812 A1 | 12/1991 |
|---|---|---|
| WO | WO 97/45202 A1 | 12/1997 |
| WO | WO 99/15321 A1 | 4/1999 |
| WO | WO 99/35500 A1 | 7/1999 |
| WO | WO 99/53304 A1 | 10/1999 |
| WO | WO 00/05338 A1 | 2/2000 |
| WO | WO 03/069349 A2 | 8/2003 |
| WO | WO 2004/106519 A2 | 12/2004 |
| WO | WO 2006/015260 A2 | 2/2006 |
| WO | WO 2006/063133 A2 | 6/2006 |

OTHER PUBLICATIONS

Payen et al. Intensive Care Med (2008) 34:1371-1376.*
Fontaine et al. Critical Care Medicine (2011) 39(12); 2684-2690.*
Cobb et al. Critical Care Medicine (2002) 30(12): 2711-2721.*
Buras et al. Nature Reviews, Drug Discovery (2005) 4: 854-865.*
Wong et al. Critical Care Medicine (2009) 37(5): 1558-1566.*
Payen et al. (Intensive Care Medicine 34: 1371-1376 (2008) + supplementary material.*
Pachot et al. Immunology Letters 106: 63-71 (2006).*
Prucha et al. Shock 22: 29-33 (2004).*
Rychlik, W. Methods in Molecular Biology 402: 35-59 (2007).*
Marshall, O. Methods in Molecular Biology 402: 403-414 (2007).*
Mohr et al. Trends in Molecular Medicine 13: 422-432 (2007).*
Sugiura et al. British Journal of Dermatology 152:146-149 (2005).*
Landelle et al. Infection Control and Hospital Epidemiology (2008) 29: 1054-1065.*
Textoris et al. European Journal of Anaesthesiology 2011; 28: 318-324.*
Tang et al. Critical Care 2010; 14: R237 (Year: 2010).*
Abe et al. The Journal of Immunology 2005; 174: 5837-5845 (Year: 2005).*
Daviaud et al. Timing and causes of death in septic shock. Annals of Intensive Care 2015; 5: 16 (Year: 2015).*
Lugering et al., "Immunohistochemical Distribution and Serum Levels of the Ca2+-Binding Proteins MRP8, MRP14 and Their Heterodimeric Form MRP8/14 in Crohn's Disease", Digestion 1995, vol. 56, pp. 406-414.
Sampson et al., "Hyperzincaemia and hypercalprotectinaemia: a new disorder of zinc metabolism", The Lancet, Nov. 30, 2002, vol. 360, pp. 1742-1745.
Hunter, "High Level Expression and Dimer Characterization of the S100 EF-hand Proteins, Migration Inhibitory Factor-related Proteins 8 and 14", Journal of Biological Chemistry May 15, 1998, vol. 273, No. 20, pp. 12427-12435.
Bhardwaj et al., "The calcium-binding proteins MRP8 and MRP14 form a membrane-associated heterodimer in a subset of monocytes/macrophages present in acute but absent in chronic inflammatory lesions", European Journal of Immunol. 1992, vol. 22, pp. 1891-1897.
Corbin et al., "Metal Chelation and Inhibition of Bacterial Growth in Tissue Abscesses", Science 2008, vol. 319, pp. 962-965; and Supporting Online Material (34 pages).
Kerkhoff et al., "Novel insights into structure and function of MRP8 (S100A8) and MRP14 (S100A9)", Biochimica et Biophysica Acta 1998, vol. 1448, pp. 200-211.
Novick, "Combating Impervious Bugs", Science 2008, vol. 319, pp. 910-911.
Levison et al., "New approaches to the isolation of DNA by ion-exchange chromatography", Journal of Chromatography A 1998, vol. 827, pp. 337-344.
Jul. 30, 2010 Search Report issued in International Application No. PCT/FR2010/050070 (with translation).
Jul. 30, 2011 Written Opinion of the International Searching Authority issued in International Application No. PCT/FR2010/050070 (translation only).
Jun. 9, 2009 Search Report issued in French National Registration No. 2941239 (with translation).
Jul. 14, 2009 Search Report issued in French National Registration No. 2941240 (with translation).
Apr. 1, 2014 Office Action issued in Mexican Patent Application No. MX/a/2011/007624 (English language translation only).
Leach et al., Steven T., "S100 calgranulin proteins S100A8, S100A9 and S100A12 are expressed in the inflamed gastric mucosa of Helicobacter pylori-infected children", Can J Gastroenterol, May 2008, vol. 22, No. 5, pp. 461-464.
Vandal et al., Karen, "Blockade of S100A8 and S100A9 Suppresses Neutrophil Migration in Response to Lipopolysaccharide", The Journal of Immunology, 2003, vol. 171, No. 5, pp. 2602-2609.

* cited by examiner

METHODS FOR DETERMINING A PATIENT'S SUSCEPTIBILITY OF CONTRACTING A NOSOCOMIAL INFECTION AND FOR ESTABLISHING A PROGNOSIS OF THE PROGRESSION OF SEPTIC SYNDROME

The present invention relates to a method for determining a patient's susceptibility of contracting a nosocomial infection. The invention also relates to a method for establishing a prognosis of the progression of septic shock in a patient.

Nosocomial infections constitute a real public health problem. In France, the number of patients who contract a nosocomial infection each year is estimated at between 500 000 and 800 000. The occurrence of nosocomial infections is linked to various factors, such as the medical techniques used, but also a patient's susceptibility of contracting a nosocomial infection. Thus, patients with a deficient immune system, malnourished persons, neonates, the elderly, persons with septic syndrome, patients with extensive burns, and persons in a traumatic state may be more predisposed than others to contracting a nosocomial infection.

Septic syndrome, a systemic response to infection, represents one of the primary causes of mortality in intensive care units. It may result from a bacterial, viral, mycotic or parasitic infection. Septic syndromes can be classified according to their severity. The following are distinguished, in order of increasing severity: SIRS (systemic inflammatory response syndrome), sepsis, severe sepsis and septic shock. Thus, in 2001, a group of experts proposed criteria for defining these four clinical syndromes[1]:

SIRS is an inflammatory systemic response triggered by a variety of infectious or noninfectious causes. Among SIRS states triggered by noninfectious causes, we may mention trauma states, burns, pancreatitis, and acute respiratory syndromes. An inflammatory systemic response manifested by at least two of the following signs: a) temperature above 38° C. or below 36° C.; b) heart rate above 90 beats per minute; c) breathing rate above 20 respirations per minute; d) leukocyte count above $12000/mm^3$ or below $4000/mm^3$, sepsis is a syndrome of inflammatory systemic response related to an infection, severe sepsis is a sepsis associated with arterial hypotension and/or hypoperfusion and/or dysfunction of at least one organ, septic shock is a severe sepsis associated with a persistent hypotension and can be qualified by:
  the presence of an identified infectious site,
  persistent hypotension despite adequate filling and treatment with vasopressors.

In general, the signs of sepsis, of severe sepsis and of septic shock are very similar, and the difference between these three situations resides mainly in the level of disturbance of all the vital functions. During septic shock, we mainly observe a drop in blood pressure, tachycardia, polypnea, marbling of the skin, hypo- or hyperthermia, shivering. These signs are also accompanied by dysfunction of "target" organs with a deterioration of function of organs remote from the infectious focus (kidneys, lungs, central nervous system, digestive system and blood coagulation systems) reflected in oliguria (<0.5 ml/kg/h), renal insufficiency, hypoxemia, thrombopenia, agitation, and confusion).

Patients with septic syndrome are also more or less sensitive to nosocomial infections, i.e. infections associated with a stay in a health establishment. This sensitivity has a considerable impact on the survival and good recovery of these patients.

The progression of septic syndrome from the stage of sepsis to a stage of severe sepsis, and then of septic shock is not systematic since about 64% of patients with sepsis develop severe sepsis, and 23% of patients with severe sepsis progress to septic shock. Before this final stage of septic shock, treatments must be prescribed for the patient in order to halt and reverse the physiopathological process. Thus, a satisfactory hemodynamic state must be restored and effective ventilation must be provided. There must also be simultaneous symptomatic treatment of shock and antibiotic treatment based as far as possible on the bacteriological data.

It appears that although some patients developing septic syndrome, and notably septic shock, can be resuscitated by standard management, such as broad-spectrum antibiotic treatment put in place before obtaining the results of bacteriological analyses indicating the source of infection, other patients, developing much more severe septic syndrome, require implementing intensive therapy, such as activated protein C. Apart from the very high cost, this kind of therapy exposes patients to the risk of serious undesirable effects (disorders of coagulation, etc.). It is therefore very important to effectively target patients who are likely to benefit from such treatment.

Accordingly, knowledge of the etiology of the inflammatory systemic response and determination of the susceptibility of a patient with an inflammatory systemic response for contracting a nosocomial infection are essential for proposing treatment suited to the patient. Another factor that is important for the patient is to be able to establish a prognosis of the progression of septic shock as early as possible.

To date, there is no test for determining a patient's susceptibility for developing a nosocomial infection, in particular for a patient with an inflammatory systemic response, whether or not linked to an infection. The inventors demonstrated, unexpectedly, that analysis of the expression of the genes S100A9 and/or S100A8 is particularly suitable for determination of said susceptibility and that, moreover, it is appropriate for establishing a prognosis of the progression of septic shock.

Before going any further, the following definitions are given for better understanding of the invention.

Septic syndrome means a systemic response to infection. This septic syndrome can be at a stage of SIRS, sepsis, severe sepsis or of septic shock. Preferably, the septic syndrome is septic shock.

Nosocomial infection means any infection contracted in a health establishment 48 hours after admission and that was not present on admission of the patient to said establishment.

The term target genes means the S100A9 gene and the S100A8 gene, in particular the S100A9 gene referenced in GenBank under accession number NM_002965.3 and the S100A8 gene referenced in GenBank under accession number NM_002964.3.

Expression product of the S100A9 gene and of the S100A8 gene means messenger RNA or a fragment of mRNA, cDNA or a fragment of cDNA, a protein or a protein fragment.

Biological sample means any material obtained from the patient, which may contain a biological material making it possible to detect the expression of a gene. This can notably be a sample of the patient's blood, serum, saliva or tissue or circulating cells. This biological sample is obtained by any manner of taking samples known by a person skilled in the art, such as notably a blood sample.

Biological material means any material making it possible to detect the expression of a gene, such as notably a nucleic acid or a protein, or its coding sequence. The nucleic acid can notably be an RNA (ribonucleic acid) such as an mRNA (messenger RNA). According to a preferred embodiment of the invention, the biological material is a nucleic acid, and even more preferably an mRNA.

Extraction of the biological material from the biological sample can be effected by all the protocols for extraction of nucleic acids or of proteins that are well known to a person skilled in the art.

As a guide, the nucleic acids can notably be extracted by:
 a stage of lysis of the cells present in the biological sample, in order to liberate the nucleic acids contained in the protein and/or lipid envelopes of the microorganisms (as cellular debris which disturb subsequent reactions). As examples, it is possible to use the methods of lysis as described in patent applications:
  WO-A-00/05338 regarding mixed magnetic and mechanical lysis,
  WO-A-99/53304 regarding electrical lysis, and
  WO-A-99/15321 regarding mechanical lysis.
 A person skilled in the art can use other methods of lysis that are well known, such as thermal or osmotic shock or chemical lysis by chaotropic agents such as guanidium salts (U.S. Pat. No. 5,234,809).
 a stage of purification, permitting separation of the nucleic acids from the other cellular constituents salted-out in the lysis stage. This stage generally makes, it possible to concentrate the nucleic acids. As an example, it is possible to use magnetic particles optionally coated with oligonucleotides, by adsorption or covalence (cf. U.S. Pat. Nos. 4,672,040 and 5,750,338), and thus purify the nucleic acids that have become attached to these magnetic particles, by a washing stage. This stage of purification of the nucleic acids is particularly advantageous if subsequent amplification of said nucleic acids is required. A particularly interesting embodiment of these magnetic particles is described in patent applications WO-A-97/45202 and WO-A-99/35500. Another interesting example of a method of purification of nucleic acids is the use of silica either in the form of a column, or in the form of inert particles[2] or magnetic particles (Merck: MagPrep® Silica, Promega: MagneSil™ Paramagnetic particles). Other methods that are widely used are based on ion exchange resins in column or paramagnetic particulate format (Whatman: DEAE-Magarose) (Levison P R et al., J. Chromatography, 1998, p. 337-344). Another method that is very relevant but not exclusive for the invention is that of adsorption on a metal oxide support (from the company Xtrana: XtraBind™ matrix). This stage of extraction can be carried out in automatic apparatus. The easyMAG® automatic apparatus is particularly suitable.

Specific reagent means a reagent that reacts with the biological material in order to demonstrate, directly or indirectly, the expression of a target gene, which can be determined by analysis of the mRNAs resulting from this gene, or by analysis of the protein encoded by this gene.

As a guide, when we wish to determine the expression of a target gene by analysis of the protein encoded by this gene, this specific reagent comprises at least one antibody specific to the protein encoded by this target gene.

As a guide, when we wish to determine the expression of a target gene by analysis of the mRNAs transcribed starting from this gene, this specific reagent comprises at least one amplification primer specific to the complementary DNA of this mRNA (it is then called amplification primer specific to a target gene). The DNA complementary to an mRNA can be obtained according to a protocol well known by a person skilled in the art. As a guide, the total RNAs (comprising ribosomal RNAs, transfer RNAs, mRNAs) are extracted from the biological sample. Then a reaction of reverse transcription is carried out by means of a reverse transcriptase enzyme, which makes it possible to obtain, from an RNA fragment, a complementary fragment of DNA (cDNA). The execution of such a stage is well known by a person skilled in the art. When we wish more particularly to obtain only the DNAs complementary to the messenger RNAs, this enzymatic stage is carried out in the presence of nucleotide fragments comprising only thymine bases (polyT), which hybridize by complementarity to the polyA sequence of the various mRNAs to form a polyT-polyA complex, which then serves as the starting point for the reaction of reverse transcription performed with the reverse transcriptase enzyme. Then various DNAs are obtained that are complementary to the various messenger RNAs initially present in the biological sample. Hereinafter, cDNA denotes a DNA complementary to a messenger RNA.

Amplification primer means a nucleotide fragment with from 5 to 100 nucleotide units, preferably from 15 to 25 nucleotide units and possessing specificity of hybridization in determined conditions for initiation of enzymatic polymerization, for example in an enzymatic amplification reaction.

Enzymatic amplification reaction means a process generating multiple copies of a target nucleotide fragment by means of specific amplification primers by the action of at least one enzyme. These amplification reactions are well known to a person skilled in the art and we may mention notably the following techniques: PCR (Polymerase Chain Reaction), LCR (Ligase Chain Reaction), RCR (Repair Chain Reaction), 3SR (Self Sustained Sequence Replication) with patent application WO-A-90/06995, NASBA (Nucleic Acid Sequence-Based Amplification), and TMA (Transcription Mediated Amplification) with U.S. Pat. No. 5,399,491.

The term amplicons then denotes the polynucleotides generated by a technique of enzymatic amplification. Preferably, when the enzymatic amplification is a PCR, the specific reagent comprises at least 2 specific amplification primers in order to amplify a particular region of the DNA complementary to the mRNA resulting from the target gene. When the enzymatic amplification is a PCR that is carried out after a reaction of reverse transcription, this is called RT-PCR.

Hybridization probe means a nucleotide fragment comprising 5 to 100 nucleotide units, notably from 6 to 35 nucleotide units, possessing a specificity of hybridization in specified conditions to form a hybridization complex with a target nucleotide fragment. In the present invention, the target nucleotide fragment can be a nucleotide sequence comprised in a messenger RNA or a nucleotide sequence comprised in a complementary DNA obtained by reverse transcription of said messenger RNA.

Hybridization means the process during which, in suitable conditions, two nucleotide fragments, such as for example a hybridization probe and a target nucleotide fragment, having sufficiently complementary sequences, are able to form a double strand with stable and specific hydrogen bonds. A nucleotide fragment "capable of hybridizing" to a polynucleotide is a fragment that can hybridize to said polynucleotide in conditions of hybridization that can be determined in each case in a known manner. The conditions of hybridization are determined by the stringency, i.e. the rigor of the operating conditions. Hybridization becomes increasingly specific as it is carried out with increasing stringency. Stringency is defined notably as a function of the base composition of a probe/target duplex, as well as by the degree of mismatch between two nucleic acids. Stringency can also be a function of the reaction parameters, such as concentration and type of ionic species present in the hybridization solution, nature and concentration of the denaturing agents and/or the hybridization temperature. The stringency of the conditions in which a hybridization reaction must be carried out will mainly depend on the hybridization probes used. All these data are well known and the appropriate conditions can be determined by a person skilled in the art. In general, depending on the length of the hybridization probes used, the temperature for the hybridization reaction is between about 20 and 70° C., in particular between 35 and 65° C. in a saline solution at a concentration of about 0.5 to 1 M. A stage of detection of the hybridization reaction is then carried out.

Detection means either direct detection by a physical method, or a method of detection by means of a marker. There are numerous methods for detecting nucleic acids[4, 5].

Marker means a tracer capable of producing a signal. A nonlimiting list of these tracers comprises enzymes that produce a signal detectable for example by colorimetry, fluorescence or luminescence, such as horseradish peroxidase, alkaline phosphatase, betagalactosidase, glucose-6-phosphate dehydrogenase; chromophores such as fluorescent, luminescent or staining compounds; electron density groups detectable by electron microscopy or from their electrical properties such as conductivity, by methods of amperometry or of voltammetry, or by measurement of impedance; groups detectable by optical methods such as diffraction, surface plasmon resonance, variation of contact angle or by physical methods such as atomic force spectroscopy, the tunnel effect, etc.; radioactive molecules such as $^{32}P$, $^{35}S$ or $^{125}I$. Thus, the polynucleotide can be labeled during the stage of enzymatic amplification, for example using a triphosphate nucleotide labeled for the amplification reaction. The labeled nucleotide will be a deoxyribonucleotide in the amplification systems generating a DNA, such as PCR, or a ribonucleotide in amplification techniques generating an RNA, such as the TMA or NASBA techniques. The polynucleotide can also be labeled after the stage of amplification, for example by hybridizing a probe labeled according to the sandwich hybridization technique described in document WO-A-91/19812.

In the sense of the present invention, the hybridization probe can be a so-called capture probe. In this case, the target nucleotide fragment can be labeled beforehand by means of a marker. The so-called capture probe is immobilized or immobilizable on a solid support by any suitable means, i.e. directly or indirectly, for example by covalence or adsorption. Then a hybridization reaction is carried out between said detection probe and the labeled target nucleotide fragment.

The hybridization probe can also be a so-called detection probe. In this case, the hybridization probe can be labeled by means of a marker. Then a hybridization reaction is carried out between said capture probe and the labelled target nucleotide fragment. Whether a so-called capture probe or a so-called detection probe is used, the hybridization reaction can be carried out on a solid support, which includes all materials on which a nucleic acid can be immobilized. Synthetic materials or natural materials, optionally chemically modified, can be used as the solid support, notably polysaccharides such as materials based on cellulose, for example paper, cellulose derivatives such as cellulose acetate and nitrocellulose or dextran, polymers, copolymers, notably based on monomers of the styrene type, natural fibers such as cotton, and synthetic fibers such as nylon; mineral materials such as silica, quartz, glasses, ceramics; latexes; magnetic particles; metal derivatives, gels etc. The solid support can be in the form of a microtitration plate, a membrane as described in application WO-A-94/12670, a particle or a biochip.

In the present invention, determination of expression of the S100A9 gene and of the S100A8 gene can be analyzed by the expression of the mRNAs that are transcribed at a given time. In this case, the biological material is a nucleic acid, and the specific reagent can be indiscriminately an amplification primer or a hybridization probe as defined previously.

The expression of a target gene can be determined as follows:
1) after extracting the total RNAs from a biological sample, a stage of reverse transcription is performed, as described previously, in order to obtain the various DNAs complementary to the various messenger RNAs initially present in the biological sample (or cDNA)
2) the cDNAs are amplified specifically. In this case, the specific reagent used comprises at least one amplification primer specific to the target gene, as defined previously. This stage can notably be carried out by an amplification reaction of the PCR type or by any other suitable amplification technique.
3) the expression of the target gene is determined by quantifying the cDNAs. The cDNAs can be quantified notably by using a quantification range obtained by a reaction of amplification carried out to saturation. To take into account the variability of enzymatic efficacy that may be observed during the various stages (reverse transcription, PCR, etc.), the expression of the target gene of the different groups of patients can be standardized by simultaneous determination of the expression of a so-called housekeeping gene, whose expression is similar in the different groups of patients. By finding the ratio of the expression of the target gene to the expression of the housekeeping gene, any variability between the different experiments is thus corrected. A person skilled in the art can notably refer to the following publications[6, 7].

The expression of a target gene can also be determined as follows:
1) after extracting the total RNAs from a biological sample, carry out a stage of reverse transcription, as described previously, to obtain the various DNAs complementary to the various messenger RNAs initially present in the biological sample (or cDNA)
2) immobilize the cDNAs on a membrane
3) determine the expression of the target gene by hybridizing the cDNAs to previously labeled hybridization probes specific to the target gene. These hybridization techniques are well known by a person skilled in the art, and we may mention notably Northern blotting. This hybridization reaction can be carried out after a stage of specific amplification of the DNAs complementary to the messenger RNAs of a target gene notably when the gene is weakly expressed.

The expression of a target gene can also be analyzed by the expression of the proteins encoded by the target gene. In this case, the biological material is a protein and several techniques of detection with or without ligand can be used. Mass spectrometry can be used as the technique for detection without a ligand. The specific reagent can be an antibody specific to the protein encoded by the target gene for a system of detection with a ligand.

Recombinant antibodies, specific to the protein translated by the target gene, can be obtained according to conventional methods known by a person skilled in the art, from prokaryotic organisms, such as bacteria, or from eukaryotic organisms, such as yeasts, cells of mammals, of plants, of insects or of animals, or by systems of extracellular production.

Monoclonal antibodies can be prepared according to conventional techniques known by a person skilled in the art such as the hybridoma technique, the general principle of which is recalled hereunder.

Firstly, an animal, generally a mouse (or cells in culture within the scope of immunizations in vitro) is immunized with a target antigen of interest, the B lymphocytes of which are then capable of producing antibodies to said antigen. These antibody-producing lymphocytes are then fused with "immortal" myeloma cells (murine in the example) to generate hybridomas. From the heterogeneous mixture of cells thus obtained, cells are then selected that are capable of producing a particular antibody and of multiplying indefinitely. Each hybridoma is multiplied in the form of a clone, each leading to the production of a monoclonal antibody, whose properties of recognition with respect to the antigen of interest can be tested for example by ELISA, by immunotransfer in one or two dimensions, by immunofluorescence, or by means of a biosensor. The monoclonal antibodies thus selected are then purified, notably by affinity chromatography. Antibody fragments can for example be obtained by proteolysis. Thus, they can be obtained by enzymatic digestion, resulting in fragments of the Fab type (treatment with papain[8]) or of the F(ab)'2 type (treatment with pepsin[9]). They can also be prepared by recombinant methods[10]. Another antibody fragment that is suitable for the purposes of the invention comprises an Fv fragment, which is a dimer constituted of the noncovalent association of the variable light domain (VL) and the variable heavy domain (VH) of the Fab fragment, therefore of an association of two polypeptide chains. In order to improve the stability of the Fv fragment due to dissociation of the two polypeptide chains, this Fv fragment can be modified by genetic engineering by inserting a suitable peptide bond between domain VL and domain VH[11]. This is then called scFv ("single chain Fragment variable") as it is constituted of a single polypeptide chain. The use of a peptide bond preferably composed of 15 to 25 amino acids makes it possible to connect the C-terminal end of a domain to the N-terminal end of the other domain, thus constituting a monomer molecule endowed with binding properties similar to those of the antibody in its complete form. The two orientations of the VL and VH domains are suitable (VL-link-VH and VH-link-VL) as they have identical functional properties. Of course, any fragment known by a person skilled in the art and having the immunological characteristics defined above is suitable for the purposes of the invention.

When the biological material is a protein resulting from expression of a gene, the expression of the latter can be determined by detecting and or quantifying said protein by Western slot or ELISA, or any other method known by a person skilled in the art, such as a method of chemiluminescence based on the biological material.

The ELISA technique ("Enzyme Linked Immuno Sorbent Assay") is an immunoenzymatic assay on a solid support. This test falls within the more general scope of EIAs ("Enzyme Immunoassays") in which the assay is coupled to an enzyme-catalyzed reaction. The technique uses one or two antibodies. The antibody for detecting the formation of immune complexes (antigen/antibody) is coupled to the enzyme and can generate the emission of a signal by a chromogenic or fluorogenic substrate.

Western Blotting is a test for detecting a specific protein in a sample by means of an antibody specific to this protein, comprising the following stages as described hereunder.

The first stage is gel electrophoresis, which makes it possible to separate the proteins of the sample according to their size.

The proteins in the gel are then transferred onto a membrane (nitrocellulose, PVDF etc.) by pressure or by application of an electric current, the proteins becoming fixed on the membrane through hydrophobic and ionic interactions.

After saturation of the sites of nonspecific interaction, a first antibody specific to the protein to be investigated (primary antibody) is incubated with the membrane.

The membrane is then rinsed to remove the unbound primary antibodies, then incubated with so-called secondary antibodies, which will bind to the primary antibodies. This secondary antibody is usually bound to an enzyme that permits visual identification of the protein under investigation on the membrane. Addition of a substrate labeled with the enzyme produces a colored reaction which is visible on the membrane.

By analyzing the expression of the S100A9 gene and/or of the S100A8 gene, it is possible to determine a patient's susceptibility of contracting a nosocomial infection, in particular of a patient with an inflammatory systemic response, and to establish a prognosis of the progression of a septic syndrome. It is possible for example to analyze the expression of at least one target gene in a patient whose susceptibility of contracting a nosocomial infection is unknown, and by comparing with known values of the average expression of the target gene of patients who are sensitive and known values of average expression of the target gene of patients who are not sensitive, determine whether the patient is likely to contract a nosocomial infection. In the same way, it is possible for example to analyze the expression of at least one target gene and by comparing with averages of known expression of the target gene, establish a prognosis of the progression of a septic syndrome, including a prognosis of survival or of death.

The invention therefore relates to a method for determining a patient's susceptibility of contracting a nosocomial infection according to which:

a) a biological sample is obtained from a patient and the biological material is extracted from the biological sample b) at least one specific reagent of an expression product of at least one target gene selected from the S100A9 and S100A8 target genes is prepared c) the expression of at least one of the target genes S100A9 and S100A8 is determined, overexpression relative to a specified threshold value being an indication of susceptibility of contracting a nosocomial infection.

In stage c), it is possible to determine the expression of the S100A9 target gene and of the S100A8 target gene, overexpression of the S100A9 target gene relative to a specified threshold value and overexpression of the S100A8 target gene relative to a specified threshold value being an indication of susceptibility of contracting a nosocomial infection.

A person skilled in the art possesses various possible ways of determining a threshold value. As an example we may mention determination of Youden's index.

Youden's index corresponds to a measure of the overall degree of non-error. It varies between 0, for a test not permitting discrimination of two populations, and 1, for a test permitting perfect discrimination of two populations. The maximum of Youden's index corresponds to the threshold value for which the number of false results (false negative or false positive) is the lowest. The closer Youden's index is to 1, the better the diagnostic performance[12].

In particular, the biological sample is taken from a patient with an inflammatory systemic response, whether or not associated with an infection. The biological sample can be a blood sample and the biological material extracted can be, among other things, a nucleic acid. Preferably, the total RNAs are extracted from the biological sample and the expression of the target gene is determined by analysis of the expression of the mRNAs.

In a preferred embodiment of the method of the invention the specific reagent comprises at least one amplification primer or at least one hybridization probe specific to the expression product of the S100A9 target gene and/or of the S100A8 target gene; or at least one antibody specific to the expression product of the S100A9 target gene and/or of the S100A8 target gene.

The method is notably suitable for determining the susceptibility of contracting a nosocomial infection for a patient with septic syndrome, i.e. who has an inflammatory systemic response to an infection, such as SIRS, sepsis, severe sepsis and septic shock.

The reagent specific to an expression product of the S100A9 gene and/or of the S100A8 gene is therefore used for determining a patient's susceptibility of contracting a nosocomial infection, in particular for a patient with an inflammatory systemic response, whether or not associated with an infection. The reagent can comprise at least one hybridization probe specific to the S100A9 target gene, at least one hybridization probe specific to the S100A8 target gene, at least one amplification primer specific to the S100A9 target gene, at least one amplification primer specific to the S100A8 target gene, at least one antibody specific to the molecule S100A9 or at least one antibody specific to the molecule S100A8.

Analysis of expression of the S100A9 and/or S100A8 gene also makes it possible to establish a prognosis of the progression of septic syndrome (prognosis including survival and death).

Thus, the invention proposes a method for establishing a prognosis of the progression of septic syndrome in a patient, according to which:
  a) a biological sample is obtained from a patient and the biological material is extracted from the biological sample
  b) at least one specific reagent of an expression product of at least one target gene selected from the S100A9 and S100A8 target genes is prepared
  c) the expression of at least one of the target genes S100A9 and S100A8 is determined, underexpression relative to a specified threshold value being an indication of a good prognosis of the progression of septic syndrome and overexpression relative to a specified threshold value being an indication of a poor prognosis of the progression of septic syndrome.

In stage c), it is possible to determine the expression of the S100A9 target gene and of the S100A8 target gene, underexpression of the S100A9 target gene relative to a specified threshold value and underexpression of the S100A8 target gene relative to a specified threshold value being an indication of a good prognosis of the progression of septic syndrome;

overexpression of the S100A9 target gene relative to a specified threshold value and overexpression of the S100A8 target gene relative to a specified threshold value relative to a specified threshold value being an indication of a poor prognosis of the progression of septic syndrome.

It is within the capacity of a person skilled in the art to determine a threshold value. We may mention as an example determination of Youden's index. Youden's index corresponds to a measure of the overall degree of non-error. It varies between 0, for a test not permitting discrimination of two populations, and 1, for a test permitting perfect discrimination of two populations. The maximum of Youden's index corresponds to the threshold value for which the number of false results (false negative or false positive) is the lowest. The closer Youden's index is to 1, the better the diagnostic performance[12].

The biological sample can be a blood sample and the biological material extracted can be, among other things, a nucleic acid. Preferably, the total RNAs are extracted from the biological sample and the expression of the target gene is determined by analysis of the expression of the mRNAs.

In a preferred embodiment of the method of the invention the specific reagent comprises at least one amplification primer or at least one hybridization probe specific to the expression product of the S100A9 target gene and/or of the S100A8 target gene; or at least one antibody specific to the expression product of the S100A9 target gene and/or of the S100A8 target gene.

The reagent specific to an expression product of the S100A9 gene and/or of the S100A8 gene is therefore used for establishing a prognosis of the progression of septic syndrome in a patient (including a prognosis of survival or of death). The reagent can comprise at least one hybridization probe specific to the S100A9 target gene, at least one hybridization probe specific to the S100A8 target gene, at least one amplification primer specific to the S100A9 target gene, at least one amplification primer specific to the S100A8 target gene, at least one antibody specific to the molecule S100A9 or at least one antibody specific to the molecule S100A8.

EXAMPLES

Example 1

Investigation of Expression of the S100A9 Gene

Test Samples

A group of 44 healthy volunteers (S) and a group of 148 patients with septic syndrome (SEP); sampled on D1, D2 or D3 after septic shock (H0 being injection of the vasopressor treatment), were used, for comparing the expression of the S100A9 gene in the peripheral blood. A group of 44 healthy patients (S) and a group of 148 patients developing septic shock (SEP) were identified.

Extraction of the RNAs and Synthesis of the cDNAs

For each patient, the biological sample was a blood sample, obtained regularly during the first 10 days following the onset of septic syndrome developed by the patients SEP. Sampling was also carried out by an identical protocol in healthy patients (S). These samples were collected directly in PAXgene™ Blood RNA tubes (PreAnalytiX, Frankin Lakes, USA).

After the blood sampling stage and in order to obtain complete lysis of the cells, the tubes were left at room temperature for 4 h and then stored at −20° C. until extraction of the biological material. More precisely, in this protocol, the total RNAs were extracted by means of PAXgene Blood RNA® kits (PreAnalytiX) following the manufacturer's recommendations. Briefly, the tubes were centrifuged (10 min, 3000 g) to obtain a pellet of nucleic acids. This pellet was washed and taken up in a buffer containing proteinase K required for digestion of the proteins (10 min at 55° C.). A repeat centrifugation (5 min, 19000 g) was carried out to remove the cellular debris, and ethanol was added in order to optimize the conditions for fixation of the nucleic acids. The total RNAs were specifically fixed on the columns PAXgene RNA spin column and, before elution of the latter, digestion of the contaminating DNA was carried out using the RNAse free DNAse Set™ (Qiagen Ltd, Crawley, UK).

For each extraction, the quality of the total RNAs was verified by capillary electrophoresis using the RNA 6000 Nano Chip™ kit (Agilent technologies). The instrument used is the bioanalyzer 2100. A reverse transcription (RT) reaction was carried out in a final volume of 20 μl. The total RNA (0.5 μg) was mixed with 1 μl of polyT at 50 μM and 1 μL of annealing buffer and was then incubated for 5 min at 65° C. After cooling in ice, the solution was mixed with 10 μl of 2× First Strand Reaction. Mix and 2 μL of SuperScript III/RNase™ out enzyme Mix RT (15 U/μl), all these products being obtained from the SuperScript First Strand Synthesis Super Mix™ RT-PCR system (Invitrogen). Reverse transcription was carried out for 50 min at 50° C. and then stopped by incubation for 5 min at 85° C. Finally, each solution of cDNA was diluted to 1/10 in DEPC water.

Preparation of Standard Ranges for Quantification

Starting from a pool of cDNA obtained from healthy subjects, amplification of the 153-179 region of the S100A9 target gene (GenBank No. NM_002965.3) was performed by PCR (Polymerase Chain Reaction), conducted to saturation, using the following primer pair:

Sense primer:
5'-TCAAAGAGCTGGTGCGAAAA-3' (SEQ ID NO: 1)

Antisense primer:
5'-AACTCCTCGAAGCTCAGCTG-3' (SEQ ID NO: 2)

Analysis of Expression of the mRNAs by Real-Time PCR

The mRNAs of the S100A9 target gene retranscribed to cDNA, as described above, were quantified by real-time quantitative PCR using the LightCycler™ (Roche). The PCR reactions were carried out using the Fast-Start™ DNA Master SYBR Green I real-time PCR kit (Roche Molecular Biochemicals). Each PCR was performed in a final volume of 20 μl containing 3.6 μl of water, 2.4 μl of $MgCl_2$, 2 μl of SYBR Green mix (Fast-Start™ DNA master SYBR green dye+Taq DNA polymerase) and 10 of each primer (10 μM) and 10 μl of cDNA solution. The primers used are those described previously. After a stage of denaturation of 10 min at 95° C., amplification is carried out by 40 cycles of a "touch-down" PCR protocol (10 s at 95° C., 10 s of hybridization at 68-58° C., followed by extension of 16 s at 72° C.). At the end of each cycle, the fluorescence emitted by the SYBR Green dye was measured.

To confirm the specificity of amplification, the PCR products were systematically submitted to analysis of the melting curve (LightCycler™—Roche). For this, the PCR products were treated at a temperature increasing from 58 to 98° C. with a rate of increase of 0.1° C./s. For each PCR product, a single peak was obtained during analysis of the curve, characterized by a specific melting temperature.

The combination of primers required for quantification of the housekeeping gene CPB was supplied by Search-LC (Heidelberg, Germany; reference 488116).

The amount of target mRNA relative to the amount of mRNA of the housekeeping gene cyclophilin B was analyzed by the relative quantification technique with the LightCycler Relative Quantification Software™ (Roche Molecular Biochemicals). The "Second Derivative Maximum Method" of the LightCycler™ software (Roche) was used for automatically determining the "Crossing Point" (Cp) for each sample. The value of Cp was defined as the number of cycles for which the fluorescence was significantly different from the background noise.

Five serial dilutions at 1/10 were performed in quadruplicate with each standard in order to generate a calibration curve expressing Cp as a function of the logarithm of the copy number. The standard dilutions were optimized so that the calibration curve covered the level of expression expected for the target gene and the housekeeping gene. The relative standard curves describing the effectiveness of PCR for the target gene and the housekeeping gene were generated and were used for performing quantification with the LightCycler Relative Quantification Software (Roche Molecular Biochemicals).

Results Obtained

The results obtained are presented in Table 1 below.

TABLE 1

| Patients | N | Median | Lower quartile | Upper quartile |
|---|---|---|---|---|
| S | 44 | 1.46 | 1.065 | 1.87 |
| SEP | 148 | 16.62 | 11.87 | 25.835 |

The p_value of the Mann-Whitney test between the healthy subjects and the patients with septic shock is <0.0001.

The expression of the marker S100A9 over the first 3 days of septic shock was significantly overexpressed relative to the healthy donors.

Example 2

Investigation of Expression of the S100A8 Gene

Test Samples

A group of 32 healthy volunteers (S) and a group of 86 patients with septic syndrome (SEP), sampled between D7 and D10 after septic shock (H0 being injection of the vasopressor treatment), were used in order to compare expression of the S100A8 gene in the peripheral blood. A group of 32 healthy patients (S) and a group of 86 patients developing septic shock (SEP) were identified.

Extraction of the RNAs and Synthesis of the cDNAs

For each patient, the biological sample is a blood sample, regularly obtained during the first 10 days following the onset of septic syndrome developed by the SEP patients. Sampling was also carried out according to an identical protocol in healthy patients (S). These samples were collected directly in PAXgene™ Blood RNA tubes (PreAnalytiX, Frankin Lakes, USA).

After the stage of collecting blood samples and in order to obtain complete lysis of the cells, the tubes were left at room temperature for 4 h and then stored at −20° C. until extraction of the biological material. More precisely, in this protocol, the total RNAs were extracted by means of PAXgene Blood RNA® kits (PreAnalytiX) following the manufacturer's recommendations. Briefly, the tubes were centrifuged (10 min, 3000 g) to obtain a pellet of nucleic acids. This pellet was washed and taken up in a buffer containing proteinase K required for digestion of the proteins (10 min at 55° C.). A repeat centrifugation (5 min, 19000 g) was carried out to remove the cellular debris, and ethanol was added in order to optimize the conditions for fixation of the nucleic acids. The total RNAs were specifically fixed on the columns PAXgene™ RNA spin column and, before elution of the latter, digestion of the contaminating DNA was carried out using the RNAse free DNAse Set™ (Qiagen Ltd, Crawley, UK).

For each extraction, the quality of the total RNAs was verified by capillary electrophoresis using the RNA 6000 Nano Chip™ kit (Agilent technologies). The instrument used is the bioanalyzer 2100. A reverse transcription (RT) reaction was carried out in a final volume of 20 μl. The total RNA (0.5 μg) was mixed with 1 μl of polyT at 50 μM and 1 μL of annealing buffer and was then incubated for 5 min at 65° C. After cooling in ice, the solution was mixed with 10 μl of 2× First Strand Reaction Mix and 2 μL of Superscript III/RNase™ out enzyme Mix RT (15 U/μl), all these products being obtained from the Superscript First Strand Synthesis Super Mix TM RT-PCR system (Invitrogen). Reverse transcription was carried out for 50 min at 50° C. and then stopped by incubation for 5 min at 85° C. Finally, each solution of cDNA was diluted to 1/10 in DEPC water.

Preparation of Standard Ranges for Quantification

Starting from a pool of cDNA obtained from healthy subjects, amplification of region 129-280 of the S100A8 target gene (GenBank No. NM_002964.3) was performed by PCR (Polymerase Chain Reaction), conducted to saturation, using the following primer pair:

Sense primer:
5'-ATTTCCATGCCGTCTACAGG-3'    (SEQ ID NO: 3)

Antisense primer:
5'-CACCAGAATGAGGAACTCCT-3'    (SEQ ID NO: 4)

Analysis of Expression of the mRNAs by Real-Time PCR

The mRNAs of the S100A8 target gene retranscribed to cDNA, as described above, were quantified by real-time quantitative PCR using the LightCycler™ (Roche). The PCR reactions were carried out using the Fast-Start™ DNA Master SYBR Green I real-time PCR kit (Roche Molecular Biochemicals). Each PCR was performed in a final volume of 20 μl containing 3.6 μl of water, 2.4 μl of $MgCl_2$, 2 μl of SYBR Green mix (Fast-Start™ DNA master SYBR green dye+Taq DNA polymerase) and 10 of each primer (10 μM) and 10 μl of cDNA solution. The primers used are those described previously. After a stage of denaturation of 10 min at 95° C., amplification is carried out by 40 cycles of a "touch-down" PCR protocol (10 s at 95° C., 10 s of hybridization at 68-58° C., followed by extension of 16 s at 72° C.). At the end of each cycle, the fluorescence emitted by the SYBR Green dye was measured.

To confirm the specificity of amplification, the PCR products were systematically submitted to analysis of the melting curve (LightCycler™—Roche). For this, the PCR products were treated at a temperature increasing from 58 to 98° C. with a rate of increase of 0.1° C./s. For each PCR product, a single peak was obtained during analysis of the curve, characterized by a specific melting temperature.

The combination of primers required for quantification of the housekeeping gene CPB was supplied by Search-LC (Heidelberg, Germany; reference 488116).

The amount of target mRNA relative to the amount of mRNA of the housekeeping gene cyclophilin B was analyzed by the relative quantification technique with the LightCycler Relative Quantification Software™ (Roche Molecular Biochemicals). The "Second Derivative Maximum Method" of the LightCycler™ software (Roche) was used for automatically determining the "Crossing Point" (Cp) for each sample. The value of Cp was defined as the number of cycles for which the fluorescence was significantly different from the background noise.

Five serial dilutions at 1/10 were performed in quadruplicate with each standard in order to generate a calibration curve expressing Cp as a function of the logarithm of the copy number. The standard dilutions were optimized so that the calibration curve covered the level of expression expected for the target gene and the housekeeping gene. The relative standard curves describing the effectiveness of PCR for the target gene and the housekeeping gene were generated and were used for performing quantification with the LightCycler Relative Quantification Software (Roche Molecular Biochemicals).

Results Obtained

The results obtained are presented in Table 2 below.

TABLE 2

| Patients | N | Median | Lower quartile | Upper quartile |
|---|---|---|---|---|
| S | 32 | 12.9 | 8.5 | 20.4 |
| SEP | 86 | 183.5 | 96.6 | 438.5 |

The p_value of the Mann-Whitney test between the healthy subjects and the patients with septic shock is <0.0001.

The expression of the S100A8 marker on days D7 to D10 after septic shock was significantly overexpressed relative to the healthy donors.

Example 3

Investigation of the Survival Prognosis Value of S100A8 in Patients with Septic Shock Test Samples The study was conducted on a cohort of 86 patients who had developed septic shock, and had been admitted to a Surgical or Medical intensive care unit of the Lyon-Sud hospital center. Samples were collected from these patients on D7, D8, D9 or D10 after septic shock (H0 being the start, of vasopressor treatment).

Extraction of the RNAs and Synthesis of the cDNAs

For each patient, the biological sample is a blood sample, which was taken daily for the first 10 days following the onset of septic syndrome (patients SEP). These samples were collected directly in PAXgene™ Blood RNA tubes (PreAnalytiX, Frankin Lakes, USA).

After the stage of collecting blood samples and in order to obtain complete lysis of the cells, the tubes were left at room temperature for 4 hours and then stored at −20° C. until extraction of the biological material. More precisely, in this protocol, the total RNAs were extracted by means of PAXgene Blood RNA® kits (PreAnalytiX) following the manufacturer's recommendations. Briefly, the tubes were centrifuged (10 min at 3000 g) to obtain a pellet of nucleic acids. This pellet was washed and taken up in a buffer containing proteinase K required for digestion of the proteins (10 min at 55° C.). A repeat centrifugation (5 min at 19000 g) was carried out to remove the cellular debris, and ethanol was added in order to optimize the conditions for fixation of the nucleic acids. The total RNAs were specifically fixed on columns PAXgene RNA Spin Column™ and, before elution of the latter, digestion of the contaminating DNA was carried out using the RNAse free DNAse Set™ (Qiagen Ltd, Crawley, UK).

For each extraction, the quality of the total RNAs was verified by capillary electrophoresis using the RNA 6000 Nano Chip™ kit (Agilent technologies). The instrument used is the bioanalyzer 2100™. A reverse transcription (RT) reaction was carried out in a final volume of 20 µl. The total RNA (0.5 µg) was mixed with 1 µl of oligo (dT) 50 µM and 1 µL of annealing buffer and was then incubated for 5 min at 65° C. After cooling in ice, the solution was mixed with 10 µl of 2× First Strand Reaction Mix and 2 µL of SuperScript III/RNase out enzyme Mix RT (15 U/µl), all these products being obtained from the Superscript First Strand Synthesis Super Mix™ RT-PCR system (Invitrogen). Reverse transcription was carried out for 50 min at 50° C. and then stopped by incubation for 5 min at 85° C. Finally, each solution of cDNA was diluted to 1/10 in DEPC water.

Preparation of Standard Ranges for Quantification

Starting from a pool of cDNA obtained from healthy subjects, amplification of region 129-280 of the S100A8 target gene (GenBank No. NM_002964.3) was performed by PCR (Polymerase Chain Reaction), conducted to saturation, using the following primer pair:

```
Sense primer:
5'-ATTTCCATGCCGTCTACAGG-3'       (SEQ ID NO: 3)

Antisense primer:
5'-CACCAGAATGAGGAACTCCT-3'       (SEQ ID NO: 4)
```

Analysis of Expression of the mRNAs by Real-Time Quantitative PCR

The mRNAs of the S100A8 target gene retranscribed to cDNA, as described above, were quantified by real-time quantitative PCR using the LightCycler™ 2.0 (Roche). The PCR reactions were carried out using the Fast-Start™ DNA Master SYBR Green I real-time PCR kit (Roche Molecular Biochemicals). Each PCR was performed in a final volume of 20 µl containing 3.6 µl of water, 2.4 µl of $MgCl_2$, 2 µl of SYBR Green mix (Fast-Start™ DNA master SYBR green dye+Taq DNA polymerase) and 10 of each primer (10 µM) and 10 µl of cDNA solution. The primers used are those described previously.

After a stage of denaturation of 10 min at 95° C., amplification is carried out by 40 cycles of a "touch-down" PCR protocol (10 s at 95° C., 10 s of hybridization at 68-58° C. (0.5° C./cycle), followed by extension of 16 s at 72° C.). At the end of each cycle, the fluorescence emitted by the SYBR Green dye was measured.

To confirm the specificity of amplification, the PCR products were systematically submitted to analysis of the melting curve (LightCycler™ 2.0—Roche). For this, the PCR products were treated at a temperature increasing from 58 to 98° C. with a rate of increase of 0.1° C./s. For each PCR product, a single peak was obtained during analysis of the curve, characterized by a specific melting temperature.

The combination of primers required for quantification of the housekeeping gene CPB was supplied by Search-LC (Heidelberg, Germany; reference 488116).

The amount of target mRNA relative to the amount of mRNA of the housekeeping gene cyclophilin B was analyzed by the relative quantification technique with the LightCycler Relative Quantification Software™ (Roche Molecular Biochemicals). The "Second Derivative Maximum Method" of the LightCycler™ software (Roche) was used for automatically determining the "Crossing Point" (Cp) for each sample. The value of Cp was defined as the number of cycles for which the fluorescence was significantly different from the background noise.

Five serial dilutions at 1/10 were performed in quadruplicate with each standard in order to generate a calibration curve expressing Cp as a function of the logarithm of the copy number. The standard dilutions were optimized so that the calibration curve covered the level of expression expected for the target gene and the housekeeping gene. The relative standard curves describing the effectiveness of PCR for the target gene and the housekeeping gene were generated and were used for performing quantification with the LightCycler Relative Quantification Software (Roche Molecular Biochemicals).

Analysis of the Results

Figure 2:
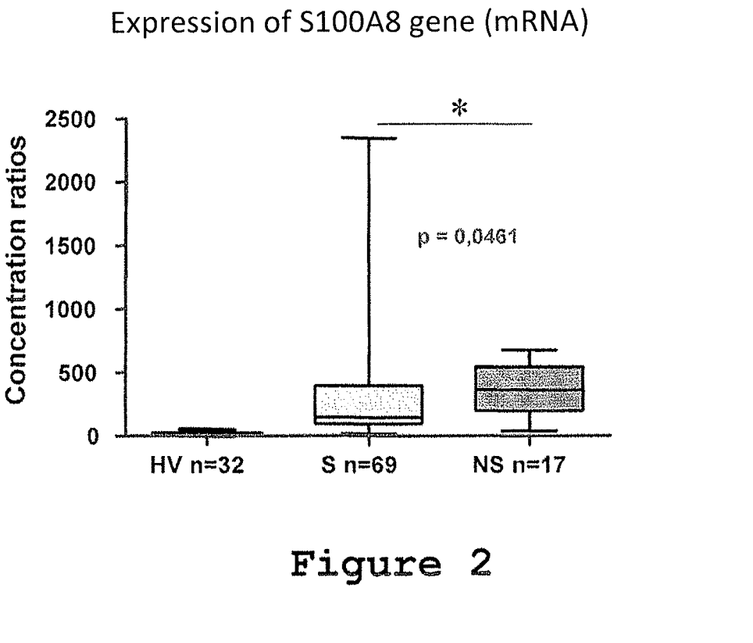
FIG. 2 illustrates the significant difference in expression of the S100A8 gene (p=0.0461) between the surviving and non-surviving patients for samples taken between D7 and D10 after the onset of septic shock. Legend: HV=healthy volunteers; S=patients surviving; NS=patients not surviving.

To determine whether expression of the S100A8 gene is correlated with patient survival, a Mann Whitney test was performed. FIG. 2 illustrates the significant difference of expression of the S100A8 gene (p=0.0461) between the surviving and non-surviving patients for the samples taken between D7 and D10 after the onset of septic shock.

Example 4

Investigation of Expression of the S100A9 Gene for Determining Patients' Susceptibility of Contracting a Nosocomial Infection Test Samples The study was conducted on a cohort of 93 patients who had developed septic shock, and had been admitted to a Surgical or Medical intensive care unit of the Lyon-Sud hospital center. Samples were collected from these patients on D7, D8, D9 or D10 after septic shock (H0 being the start of vasopressor treatment).

Among these patients who had developed septic shock, 27 patients contracted a nosocomial infection secondary to shock and 66 did not contract a nosocomial infection in the 53 days of observation of this cohort.

Extraction of the RNAs and Synthesis of the cDNAs

For each patient, the biological sample is a blood sample, which was regularly obtained during the first 10 days following the onset of septic syndrome (patients SEP). Samples were also taken from healthy subjects (S) according to an identical protocol. These samples were collected directly in PAXgene™ Blood RNA tubes (PreAnalytiX, Frankin Lakes, USA).

After the stage of collecting blood samples and in order to obtain complete lysis of the cells, the tubes were left at room temperature for 4 hours and then stored at −20° C. until extraction of the biological material. More precisely, in this protocol, the total RNAs were extracted by means of PAXgene Blood RNA® kits (PreAnalytiX) following the manufacturer's recommendations. Briefly, the tubes were centrifuged (10 min at 3000 g) to obtain a pellet of nucleic acids. This pellet was washed and taken up in a buffer containing proteinase K required for digestion of the proteins (10 min at 55° C.). A repeat centrifugation (5 min at 19000 g) was carried out to remove the cellular debris, and ethanol was added in order to optimize the conditions for fixation of the nucleic acids. The total RNAs were specifically fixed on columns PAXgene RNA Spin Column™ and, before elution of the latter, digestion of the contaminating DNA was carried out using the RNAse free DNAse Set™ (Qiagen Ltd, Crawley, UK).

For each extraction, the quality of the total RNAs was verified by capillary electrophoresis using the RNA 6000 Nano Chip™ kit (Agilent technologies). The instrument used is the bioanalyzer 2100™. A reverse transcription (RT) reaction was carried out in a final volume of 20 µl. The total RNA (0.5 µg) was mixed with 1 µl of polyT at 50 µM and 1 µl of oligo (dT) 50 µM and 1 µL of annealing buffer and was then incubated for 5 min at 65° C. After cooling in ice, the solution was mixed with 10 µl of 2× First Strand Reaction Mix and 2 µL of Superscript III/RNase out enzyme Mix RT (15 U/µl), all these products being obtained from the Superscript First Strand Synthesis Super Mix™ RT-PCR system (Invitrogen). Reverse transcription was carried out for 50 min at 50° C. and then stopped by incubation for 5 min, at 85° C. Finally, each solution of cDNA was diluted to 1/10 in DEPC water.

Preparation of Standard Ranges for Quantification

Starting from a pool of cDNA obtained from healthy subjects, amplification of the 153-179 region of the S100A9 target gene (GenBank No. NM_002965.3) was performed by PCR (Polymerase Chain Reaction), conducted to saturation, using the following primer pair:

```
Sense primer:
5'-TCAAAGAGCTGGTGCGAAAA-3'      (SEQ ID NO: 1)

Antisense primer:
5'-AACTCCTCGAAGCTCAGCTG-3'      (SEQ ID NO: 2)
```

Analysis of Expression of the mRNAs by Real-Time PCR

The mRNAs of the S100A9 target gene retranscribed to cDNA, as described above, were quantified by real-time quantitative PCR using the LightCycler™ (Roche). The PCR reactions were carried out using the Fast-Start™ DNA Master SYBR Green I real-time PCR kit (Roche Molecular Biochemicals). Each PCR was performed in a final volume of 20 µl containing 3.6 µl of water, 2.4 µl of $MgCl_2$, 2 µl of SYBR Green mix (Fast-Start™ DNA master SYBR green dye+Taq DNA polymerase) and 10 of each primer (10 µM) and 10 µl of cDNA solution. The primers used are those described previously. After a stage of denaturation of 10 min at 95° C., amplification is carried out by 40 cycles of a "touch-down" PCR protocol (10 s at 95° C., 10 s of hybridization at 68-58° C., followed by extension of 16 s at 72° C.). At the end of each cycle, the fluorescence emitted by the SYBR Green dye was measured.

To confirm the specificity of amplification, the PCR products were systematically submitted to analysis of the melting curve (LightCycler™—Roche). For this, the PCR products were treated at a temperature increasing from 58 to 98° C. with a rate of increase of 0.1° C./s. For each PCR product, a single peak was obtained during analysis of the curve, characterized by a specific melting temperature.

The combination of primers required for quantification of the housekeeping gene CPB was supplied by Search-LC (Heidelberg, Germany; reference 488116).

The amount of target mRNA relative to the amount of mRNA of the housekeeping gene cyclophilin B was analyzed by the relative quantification technique with the LightCycler Relative Quantification Software™ (Roche Molecular Biochemicals). The "Second Derivative Maximum Method" of the LightCycler™ software (Roche) was used for automatically determining the "Crossing Point" (Cp) for each sample. The value of Cp was defined as the number of cycles for which the fluorescence was significantly different from the background noise.

Five serial dilutions at 1/10 were performed in quadruplicate with each standard in order to generate a calibration curve expressing Cp as a function of the logarithm of the copy number. The standard dilutions were optimized so that the calibration curve covered the level of expression expected for the target gene and the housekeeping gene. The relative standard curves describing the effectiveness of PCR for the target gene and the housekeeping gene were generated and were used for performing quantification with the LightCycler Relative Quantification Software (Roche Molecular Biochemicals).

Results of Univariate and Multivariate Analyses

To determine the variables having an influence on occurrence of a nosocomial infection, a univariate analysis and then a multivariate analysis are performed. The univariate analysis is performed by effecting a logistic regression of the status attained or not attained by a nosocomial infection as a function of different variables and for the S100A9 marker in mRNA on days D7 to D10 after the onset of septic shock. Then a multivariate logistic regression is performed on the variables displaying a level of significance (p)<0.15 with the univariate analysis. The "backward" selection method (at the start, all the variables are taken into account in the model, then they are withdrawn one by one) is used with a significance threshold at 0.05. The results are presented in Table 3 below. The odds ratio (O.R.) and its 95% confidence interval are shown for each result.

TABLE 3

| | | Univariate analysis (N = 93) | | | Multivariate analysis (N = 93) | | |
|---|---|---|---|---|---|---|---|
| | | OR | 95% CI | p | OR | 95% CI | p |
| Sex | Male | 1 | — | — | | | |
| | Female | 1.6 | 0.641-3.997 | 0.3143 | | | |
| Age (years) | >65 | 1 | — | — | — | — | — |
| | ≤65 | 2.04 | 0.814-5.115 | 0.1285 | — | — | 0.1186 |
| SAPS II on admission | >51 | 1 | — | — | | | |
| | ≤51 | 1.107 | 0.450-2.723 | 0.8246 | | | |
| SOFA on admission | <10 | 1 | — | — | — | — | — |
| | ≥10 | 3.036 | 1.132-8.144 | 0.0274 | — | — | 0.1384 |
| Co-morbidities | 0 | 1 | — | — | | | |
| | ≥1 | 1.021 | 0.414-2.514 | 0.9645 | | | |
| Type of infection | Nosocomial | 1 | — | — | | | |
| | Community | 1.144 | 0.467-2.803 | 0.7682 | | | |
| Site of infection | Pulmonary | 1 | — | — | | | |
| | Abdominal | 1.735 | 0.644-4.672 | 0.3268 | | | |
| | Others | 1.172 | 0.299-4.597 | 0.8540 | | | |
| S100A9 (mRNA) | <6.1 | 1 | — | — | 1 | — | — |
| | ≥6.1 | 6.27 | 1.718-22.891 | 0.0055 | 6.242 | 1.662-23.447 | 0.0067 |

OR: Odds Ratio
CI: confidence interval
P: significance threshold

As can be seen from Table 3, multivariate analysis reveals that expression of the S100A9 marker ≥6.1 on days 7 to 10 after the onset of septic shock significantly increases the probability of occurrence of a nosocomial infection (odds ratio at 6.2).

Example 5

Investigation of Correlation of Expression of the S100A9 Gene and of Expression of the S100A8 Gene Test Samples The study was conducted on a cohort of 86 patients who had developed septic shock, and had been admitted to a Surgical or Medical intensive care unit of the Lyon-Sud hospital center. Samples were collected from these patients on D7, D8, D9 or D10 after septic shock (H0 being the start of vasopressor treatment).

Extraction of the RNAs and Synthesis of the cDNAs

For each patient, the biological sample is a blood sample, which was taken daily for the first 10 days following the onset of septic syndrome (patients SEP). These samples were collected directly in PAXgene™ Blood RNA tubes (PreAnalytiX, Frankin Lakes, USA).

After the stage of collecting blood samples and in order to obtain complete lysis of the cells, the tubes were left at room temperature for 4 hours and then stored at −20° C. until extraction of the biological material. More precisely, in this protocol, the total RNAs were extracted by means of PAXgene Blood RNA® kits (PreAnalytiX) following the manufacturer's recommendations. Briefly, the tubes were centrifuged (10 min at 3000 g) to obtain a pellet of nucleic acids. This pellet was washed and taken up in a buffer containing proteinase K required for digestion of the proteins (10 min at 55° C.). A repeat centrifugation (5 min at 19000 g) was carried out to remove the cellular debris, and ethanol was added in order to optimize the conditions for fixation of the nucleic acids. The total RNAs were specifically fixed on columns PAXgene RNA Spin Column™ and, before elution of the latter, digestion of the contaminating DNA was carried out using the RNAse free DNAse Set™ (Qiagen Ltd, Crawley, UK).

For each extraction, the quality of the total RNAs was verified by capillary electrophoresis using the RNA 6000 Nano Chip™ kit (Agilent technologies). The instrument used is the bioanalyzer 2100™. A reverse transcription (RT) reaction was carried out in a final volume of 20 μl. The total RNA (0.5 μg) was mixed with 1 μl of oligo (dT) 50 μM and 1 μL of annealing buffer and was then incubated for 5 min at 65° C. After cooling in ice, the solution was mixed with 10 μl of 2× First Strand Reaction Mix and 2 μL of SuperScript III/RNase out enzyme Mix RT (15 U/μl), all these products being obtained from the Superscript First Strand Synthesis Super MiX™ RT-PCR system (Invitrogen). Reverse transcription was carried out for 50 min at 50° C. and then stopped by incubation for 5 min at 85° C. Finally, each solution of cDNA was diluted to 1/10 in DEPC water.

Preparation of Standard Ranges for Quantification

Starting from a pool of cDNA obtained from healthy subjects, amplification of the 153-179 region of the S100A9 target gene (GenBank No. NM_002965.3) was performed by PCR (Polymerase Chain Reaction), conducted to saturation, using the following primer pair:

```
Sense primer:
5'-TCAAAGAGCTGGTGCGAAAA-3'    (SEQ ID NO: 1)

Antisense primer:
5'-AACTCCTCGAAGCTCAGCTG-3'    (SEQ ID NO: 2)
```

Starting from a pool of cDNA obtained from healthy subjects, amplification of region 129-280 of the S100A8 target gene (GenBank No. NM_002964.3) was performed by PCR (Polymerase Chain Reaction), conducted to saturation, using the following primer pair:

```
Sense primer:
5'-ATTTCCATGCCGTCTACAGG-3'    (SEQ ID NO: 3)

Antisense primer:
5'-CACCAGAATGAGGAACTCCT-3'    (SEQ ID NO: 4)
```

Analysis of Expression of the mRNAs by Real-Time Quantitative PCR

The mRNAs of the S100A9 and S100A8 target genes retranscribed to cDNA, as described above, were quantified by real-time quantitative PCR using the LightCycler™ 2.0 (Roche). The PCR reactions were carried out using the Fast-Start™ DNA Master SYBR Green I real-time PCR kit (Roche Molecular Biochemicals). Each PCR was performed in a final volume of 20 μl containing 3.6 μl of water, 2.4 μl of $MgCl_2$, 2 μl of SYBR Green mix (Fast-Start™ DNA master SYBR green dye+Taq DNA polymerase) and 10 of each primer (10 μM) and 10 μl of cDNA solution. The primers used are those described previously.

After a stage of denaturation of 10 min at 95° C., amplification is carried out by 40 cycles of a "touch-down" PCR protocol (10 s at 95° C., 10 s of hybridization at 68-58° C. (0.5° C./cycle), followed by extension of 16 s at 72° C.). At the end of each cycle, the fluorescence emitted by the SYBR Green dye was measured.

To confirm the specificity of amplification, the PCR products were systematically submitted to analysis of the melting curve (LightCycler™ 2.0—Roche). For this, the PCR products were treated at a temperature increasing from 58 to 98° C. with a rate of increase of 0.1° C./s. For each PCR product, a single peak was obtained during analysis of the curve, characterized by a specific melting temperature.

The combination of primers required for quantification of the housekeeping gene CPB was supplied by Search-LC (Heidelberg, Germany; reference 488116).

The amount of mRNA targets relative to the amount of mRNA of the housekeeping gene cyclophilin B was analyzed by the relative quantification technique with the LightCycler Relative Quantification Software™ (Roche Molecular Biochemicals). The "Second Derivative Maximum Method" of the LightCycler™ software (Roche) was used for automatically determining the "Crossing Point" (Cp) for each sample. The value of Cp was defined as the number of cycles for which the fluorescence was significantly different from the background noise.

Five serial dilutions at 1/10 were performed in quadruplicate with each standard in order to generate a calibration curve expressing Cp as a function of the logarithm of the copy number. The standard dilutions were optimized so that the calibration curves cover the level of expression expected for the target genes and the housekeeping gene. The relative standard curves describing the effectiveness of PCR for the target gene and the housekeeping gene were generated and were used for performing quantification with the LightCycler Relative Quantification Software (Roche Molecular Biochemicals).

Analysis of the Results

Figure 1:
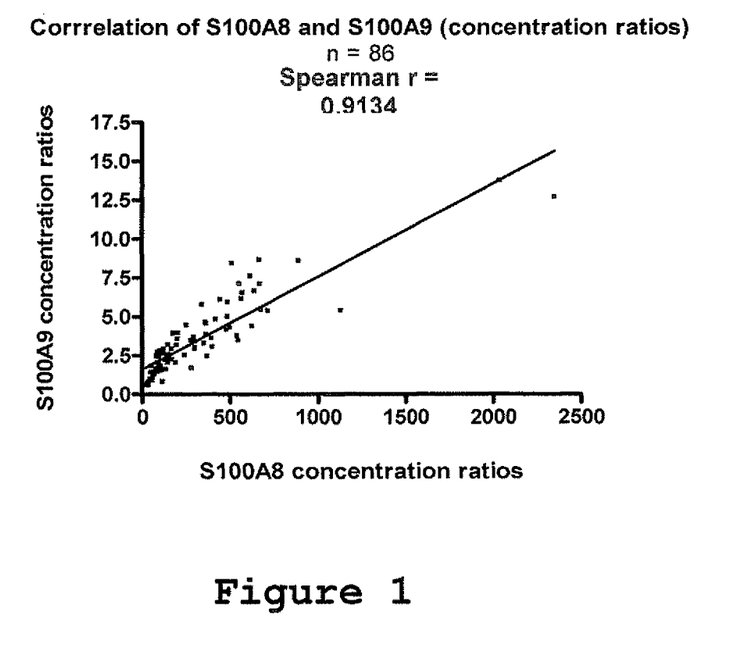
FIG. 1 presents the correlation of the gene expression of S100A8 and S100A9 (n=86). It shows the strong correlation that exists between the gene expressions of the molecules S100A9 and S100A8 with a Spearman coefficient >0.90 (r=0.9134). The gene expressions of the molecules S100A9 and S100A8 possess similar capacity for discriminating patients who are likely to contract a nosocomial infection and for establishing a prognosis of the progression of septic syndrome.

To determine whether the expression of the S100A9 gene is correlated with the expression of the S100A8 gene, a correlation analysis was performed. The results given in FIG. 1 show that there is a strong correlation between the gene expressions of these two molecules, with a Spearman coefficient >0.90. The gene expressions of the molecules S100A9 and S100A8 therefore possess a similar capacity for discriminating patients who are likely to contract a nosocomial infection and for establishing a prognosis of the progression of septic syndrome.

REFERENCES

[1] M. M. Levy, M. P. Fink, J. C. Marshall, E. Abraham, D. Angus, D. Cook, J. Cohen, S. M. Opal, J. L. Vincent and G. Ramsay, 2001 SCCM/ESICM/ACCP/ATS/SIS International Sepsis Definitions Conference, Crit. Care Med. 31 (2003), pp. 1250-1256
[2] Boom R. et al., J. Clin. Microbiol., 1990, No. 28(3), p. 495-503
[4] Kricka et al., Clinical. Chemistry, 1999, No. 45(4), p. 453-458
[5] Keller G. H. et al., DNA Probes, 2nd Ed., Stockton Press, 1993, sections 5 and 6, p. 173-249
[6] Bustin S A Journal of molecular endocrinology, 2002, 29: 23-39
[7] Giulietti A Methods, 2001, 25: 386-401
[8] Porter R R, 1959, Biochem. J., 73: 119-126
[9] Nisonoff A. et al., 1960, Science, 132: 1770-1771
[10] Skerra A., 1993, Curr. Opin. Immunol., 5: 256-262
[11] Huston P. et al., 1988, Proc. Natl. Acad. Sci. USA, 85: 5879-5883
[12] Fluss R., Faraggi D., Reiser B. (2005), "Estimation of the Youden index and its associated cutoff point". Biometrical Journal, 47:458-72

The invention claimed is:

1. A method comprising:
   a) obtaining blood samples from a human patient with septic shock at multiple time points after septic shock onset, at least one of the time points being between 7 and 10 days after septic shock onset;
   b) extracting nucleic acids from the blood samples; and
   c) measuring an overexpression of the S100A9 gene relative to a predetermined threshold value in at least the blood sample(s) obtained between 7 and 10 days after septic shock onset,
   wherein the overexpression is measured via an amplification method comprising the use of a first primer consisting of SEQ ID NO: 1 and a second primer consisting of SEQ ID NO: 2.

2. The method as claimed in claim 1, wherein RNA is the nucleic acid extracted from the blood samples, and cDNA is generated from the RNA by an amplification method.

3. The method as claimed in claim 1, wherein the amplification method is a real-time PCR amplification method.

4. The method according to claim 1, wherein septic shock is characterized by an identified infectious site and persistent hypotension.

5. A method comprising:
   a) obtaining blood samples from a human patient with septic shock at multiple time points after septic shock onset, at least one of the time points being between 7 and 10 days after septic shock onset;
   b) extracting nucleic acids from the blood samples; and
   c) measuring an overexpression of the S100A8 gene relative to a predetermined threshold value in at least the blood sample(s) obtained between 7 and 10 days after septic shock onset, the threshold value being indicative of either a healthy subject or a non-surviving septic shock patient,
   wherein the overexpression is measured via an amplification method comprising the use of a first primer consisting of SEQ ID NO: 3 and a second primer consisting of SEQ ID NO: 4.

6. The method as claimed in claim 5, wherein RNA is the nucleic acid extracted from the blood samples, and cDNA is generated from the RNA by an amplification method.

7. The method as claimed in claim 5, wherein the amplification method is a real-time PCR amplification method.

8. The method according to claim 5, wherein septic shock is characterized by an identified infectious site and persistent hypotension.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct-Amorce 1

<400> SEQUENCE: 1
tcaaagagct ggtgcgaaaa                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct-Amorce 2

<400> SEQUENCE: 2

```
aactcctcga agctcagctg                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct-S100A8

<400> SEQUENCE: 3
atttccatgc cgtctacagg                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct-S100A8

<400> SEQUENCE: 4
caccagaatg aggaactcct                                            20
```